United States Patent [19]

Hubele

[11] 4,094,990
[45] June 13, 1978

[54] CERTAIN PHYTOFUNGICIDAL N-FURANYL CARBONYL AND TETRAHYDROFURANYL CARBONYL, N-(SUBSTITUTED)PHENYL ALANINES

[75] Inventor: Adolf Hubele, Magden, Switzerland

[73] Assignee: Ciba-Geigy Corporation, Ardsley, N.Y.

[21] Appl. No.: 709,066

[22] Filed: Jul. 27, 1976

Related U.S. Application Data

[63] Continuation-in-part of Ser. No. 563,035, Mar. 28, 1975, abandoned.

[30] Foreign Application Priority Data

Apr. 2, 1974 Switzerland .......................... 4572/74
Feb. 10, 1975 Switzerland .......................... 1591/75

[51] Int. Cl.$^2$ ...................... C07D 307/68; A01N 9/28
[52] U.S. Cl. .............. 424/285; 260/256.4 R; 260/295.5 R; 260/295.5 H; 260/347.3; 260/347.4; 424/251; 424/266; 544/334; 544/335
[58] Field of Search .......................... 260/347.3, 347.4; 424/285

[56] References Cited

U.S. PATENT DOCUMENTS 2,676,188  4/1954  Bruce et al. .......................... 260/559
4,054,585  10/1977  Felaner et al. ....................... 260/347.3

*Primary Examiner*—Henry R. Jiles
*Assistant Examiner*—Bernard Dentz
*Attorney, Agent, or Firm*—Harry Falber

[57] ABSTRACT

N-acylanilides of the formula I

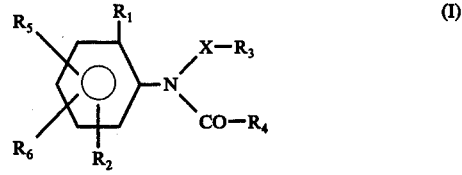

wherein the $R_4$-CO-moiety stems from the carbonic acid of an optionally halo substituted furan, tetrahydrofuran, pyridine or pyrimidine heterocycle (and wherein the remaining substituents $R_1$, $R_2$, $R_3$, $R_5$, $R_6$ and X are defined hereinafter) are effective microbicides. They are preferably used to combat phytopathogenic fungi.

17 Claims, No Drawings

CERTAIN PHYTOFUNGICIDAL N-FURANYL CARBONYL AND TETRAHYDROFURANYL CARBONYL, N-(SUBSTITUTED)PHENYL ALANINES

CROSS-REFERENCE

This application is a continuation-in-part of our application Ser. No. 563,035, filed Mar. 28, 1975, now abandoned.

The present invention provides compounds of the formula I

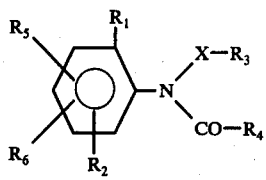

wherein $R_1$ represents alkyl of 1 to 4 carbon atoms, alkoxy of 1 to 4 carbon atoms or halogen, $R_2$ represents hydrogen, alkyl of 1 to 3 carbon atoms or halogen, $R_5$ represents hydrogen, alkyl of 1 to 3 carbon atoms or halogen, $R_6$ represents hydrogen or methyl, the total number of carbon atoms of the substituents $R_1$, $R_2$, $R_5$ and $R_6$ in the phenyl ring not exceeding 8, X represents —$CH_2$— or

$R_3$ represents —COOR' or

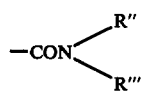

wherein each of R', R" and R''' represents hydrogen, methyl or ethyl, and $R_4$ represents an unsubstituted or a methyl- and/or halogen-substituted 5- or 6-membered heterocyclic radical with 1 or 2 heteroatoms, with the proviso that the phenyl ring contains a further substituent other than hydrogen if it is substituted in 2,6- or in 2,3,6-position by methyl and if at the same time $R_4$ represents the 2-furanyl radical and —X—$R_3$ represents the α-propionic acid methyl ester. The invention also provides a process for the manufacture of these compounds as well as compositions which contain these compounds as active substances, and a method of using these active substances as microbicidal agents.

By alkyl and alkyl moiety of an alkoxy group are meant the following groups, depending on the number of carbon atoms specified: methyl, ethyl, n-propyl, isopropyl or n-, iso-, sec.- or tert.butyl. Halogen is fluorine, chlorine, bromine or iodine.

Examples of 5- to 6-membered heterocyclic radical are: furan, bromofuran, tetrahydrofuran, bromotetrahydrofuran, pyridine, dichloropyrimidine.

German Offenlegungsschrift No. 2,006,471 teaches (2'-methylfuranyl-3')-carbonyl-2,6-dimethylaniline and (2'-methylfuranyl-3')-carbonyl-2-methyl-6-chloroaniline as active substances with moderate action against certain fungi (Uromyces phaseoli, Alternaria solani, Rhizoctonia solani).

This invention is based on the surprising observation that compounds with the markedly different structure of the formula I have what is for practical purposes a very useful microbicidal spectrum for protecting cultivated plants. Examples of cultivated plants within the scope of this invention are: cereals, maize, rice, vegetables, sugar beet, soya, ground nuts, fruit trees, ornamental plants, but primarily vines, hops, cucumber plants (cucumbers, marrows, melons), solanaceae, such as potatoes, tobacco and tomatoes, as well as bananas, cocoa and natural rubber plants.

With the active substances of the formula I it is possible to inhibit or destroy the fungi which occur in plants or parts of plants (fruit, blossoms, leaves, stems, tubers, roots) of these and related cultures of useful plants and also to protect from such fungi the parts of plants which grow later. The active substances act against the phytopathogenic fungi which belong to the following classes: ascomycetes (e.g. erysiphaceae); basidiomycetes, above all rust fungi; fungi imperfecti; but especially against oomycetes which belong to the class of phycomycetes, e.g. phytophthora, peronospora, pseudoperonospora, pythium or plasmopara. In addition, the compounds of the formula I have a systemic action. They can also be used as seed-dressing agents for protecting seeds (fruit, tubers, kernels) and plant cuttings from fungus infections as well as from phytopathogenic fungi which occur in the soil.

In a narrower sense of the meaning the invention is directed to compounds of the formula I wherein $R_1$ represents methyl, ethyl, methoxy, ethoxy or chlorine, $R_2$ is in ortho-position to the amino group and represents alkyl of 1 to 3 carbon atoms or halogen, $R_5$ represents methyl or halogen, $R_6$ represents hydrogen or methyl, the total number of carbon atoms of the substituents $R_1$, $R_2$, $R_5$ and $R_6$ in the phenyl ring not exceeding 6, X represents —$CH_2$— or

$R_3$ represents —COOR' or —CONH—R", wherein R' represents methyl or ethyl and R" represents methyl, and $R_4$ represents a 2-furanyl, 2-tetrahydrofuranyl, 5-bromo-2-furanyl, 5-bromo-2-tetrahydrofuranyl, 3-pyridyl or dichloro-5-pyrimidinyl group. The foregoing subgroup of compounds will be referred to as group Ia.

Preferred microbicides are compounds of the formula I wherein $R_1$ represents methyl, $R_2$ is in ortho-position to the amino group and represents methyl, ethyl or chlorine, —X—$R_3$ possesses the group

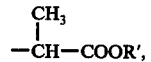

and $R_4$, $R_5$, $R_6$ and R' have the meanings previously assigned to them. These compounds will be referred to as group Ib. Preeminent among these compounds Ib are those wherein $R_4$ represents the unsubstituted 2-furanyl or 2-tetrahydrofuranyl radical which will be referred to as compounds Ic.

Within this last mentioned group Ic, especial importance attaches to microbicidal compounds wherein —X—$R_3$ represents the α-propionic acid methyl ester group and wherein the total number of carbon atoms of the substituents $R_1$, $R_2$, $R_5$ and $R_6$ does not exceed 4, for example the 2,6-dimethylaniline, 2,4,6-trimethyl-aniline or 2,3,5,6-tetramethylaniline derivatives as well as those 2,6-dimethylaniline derivatives which contain in addition a third substituent $R_5$ or $R_6$ other than hydrogen in the phenyl nucleus.

The compounds of the formula I are manufactured by acylating a compound of the formula II

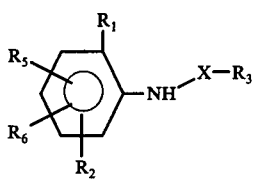

with a carboxylic acid of the formula III

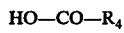   (III)

or with the acid halide, acid anhydride or ester thereof.

According to another method of the invention, it is also possible to manufacture the compounds of the formula I by converting the acyl anilide of the formula IV

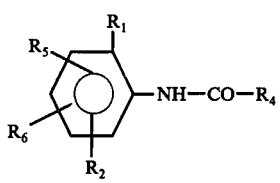

with butyl lithium or sodium hydride into the corresponding alkali salt, which is then reacted with a compound of the formula V

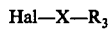   (V)

to give the desired end product, or else to react the acyl anilide of the formula IV with the compound of the formula V in the presence of an alkali carbonate (e.g. $Na_2CO_3$ or $K_2CO_3$) as proton acceptor, preferably with the addition of catalytic amounts of alkali iodide (e.g. potassium iodide).

In the formulae II, III, IV and V, the symbols $R_1$ to $R_6$ and X have the meanings assigned to them in formula I and Hal represents a halogen atom, preferably chlorine or bromine, or another easily removable radical. The term "acid halide" means preferably the acid chloride or acid bromide.

The reactions can be carried out in the presence of absence of solvents or diluents which are inert to the reactants. Examples of such solvents or diluents are: aliphatic or aromatic hydrocarbons, e.g. benzene, toluene, xylene, petroleum ether; halogenated hydrocarbons, e.g. chlorobenzene, methylene chloride, ethylene chloride, chloroform; ethers and ethereal compounds such as dialkyl ethers, dioxan, tetrahydrofuran; nitriles like acetonitrile; N,N-dialkylated amides like dimethyl formamide; anhydrous acetic acid, dimethyl sulphoxide; ketones like methyl ethyl ketone and mixtures of such solvents. The reaction temperatures are between 0° and 180° C, preferably between 20° and 120° C. In many cases it is advantageous to use acceptors or condensation agents. Suitable examples are: tertiary amines, e.g. trialkylamines (e.g. triethylamine), pyridine and pyridine bases, e.g. the oxides and hydroxides, hydrogen carbonates and carbonates of alkali metals and alkaline earth metals, as well as sodium acetate. Furthermore, it is also possible to use a surplus of the respective aniline derivative of the formula II as acid acceptor in the first method.

The process of manufacture which proceeds from compounds of the formula II can also be carried out without acid acceptors; in some instances it is expedient to pass in nitrogen in order to expel the hydrogen halide that has formed. In other instances, it is very advantageous to use dimethyl formamide as reaction catalyst.

Particulars on the manufacture of the intermediates of the formula II can be inferred from the methods which are generally indicated for the manufacture of anilinoalkane acid ester in the following publications: J. Org. Chem. 30,4101 (1965), Tetrahedron 1967, 487, Tetrahedron 1967, 493.

The compounds of the formula I in which

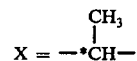

possess an asymmetrical carbonatom (*) and can be resolved into the optical antipodes in the customary manner. In this connection, the enantiomeric D-form has the more pronounced microbicidal action. Within the scope of the invention, those compounds, their agents and their use which refer to the D-configuration of the formula I are accordingly preferred. In ethanol or acetone these D-forms have, as a rule, a negative angle of rotation.

The pure, optical D-antipodes are obtained by manufacturing the racemic compound of the formula VI

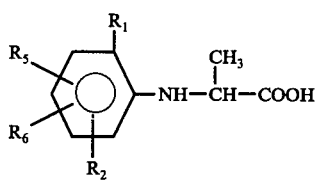

wherein $R_1$, $R_2$, $R_5$ and $R_6$ have the meanings assigned to them in formula I, and then reacting this in known manner with a nitrogen-containing, optically active base to give the corresponding salt. The pure D-form is obtained stepwise by fractional crystallisation of the salt and subsequent liberation of the acid of the formula VI which is enriched with the optical D-antipode and, if appropriate, repeating (also several times) the salt formation, crystallisation and liberation of the α-anilinopropionic acid of the formula VI. From this D-form it is then possible, if desired, to manufacture the optical D-configuration of the ester of the formula II in conventional manner, e.g. in the presence of HCl or $H_2SO_4$, with methanol or ethanol, or to manufacture the amide of the formula II with the corresponding amine of the formula HN(R'')(R'''). A suitable optically active organic base is, for example, α-phenylethylamine.

Instead of fractional crystallisation, it is also possible to obtain the enantiomeric D-form of the formula VI by replacing the hydroxy group in the naturally occurring L(+)lactic acid by halogen and reacting this product further with the desired aniline of the formula VII

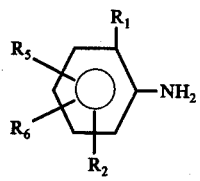
(VII)

with reversal of the configuration.

Besides the optical isomerism, an atropisomerism is normally observed about the phenyl —N< axis in those cases where the phenyl ring is substituted at least in 2,6-position and at the same time unsymmetrically to this axis (i.e. also by the presence of additional substituents as the case may be). This feature is caused by the steric hindrance of the radicals —X—$R_3$ and —CO—$R_4$. Provided no synthesis is carried out with the aim of isolating pure isomers, a product normally occurs as a mixture of two optical isomers or of two atropisomers or as a mixture of these four possible isomers. The basically better fungicidal action of the enantiomeric D-form (in comparison to the D,L-form or to the L-form) is retained however and is not noticeably affected by the atropisomerism.

The following Examples illustrate the invention in more detail but do not limit it to what is described therein. Unless otherwise stated, an active substance of the formula I, which can occur in optically active forms, is always the racemic mixture.

EXAMPLE 1

Manufacture of

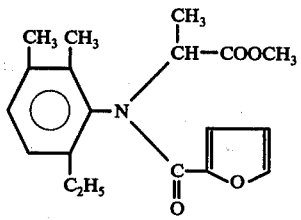

N-(1'-methoxycarbonyl-ethyl)-N-(furan-(2'')-carbonyl)-2,3-dimethyl-6-ethylaniline.

a. 100 g of 2,3-dimethyl-6-ethylaniline, 223 g of 2-bromopropionic acid methyl ester and 84 g of $NaHCO_3$ were stirred for 17 hours at 140° C. The mixture was then cooled, diluted with 300 ml of water and extraction was performed with diethyl ether. The extract was washed with a small amount of water, dried over sodium sulphate, filtered, and the ether evaporated off. After the surplus 2-bromopropionic acid methylester had been distilled off, the crude product was distilled in a high vacuum; b.p. 88°–90° C/0.04 Torr.

b. 13 g of furan-2-carboxylic acid chloride were added dropwise with stirring to 17 g of the ester obtained in (a), 2 ml of dimethyl formamide and 150 ml of absolute toluene and the mixture was refluxed for 1 hour. The solvent was evaporated off and the crude product was then crystallised by trituration with petroleum ether; m.p. 110.5°–126° C (ethyl acetate/petroleum ether). Compound 2 is the mixture of two pairs of diastereoisomers.

The D-forms of both atropisomers (compounds 2a and 2b) are obtained by acylating the D-form of α-(2,3-dimethyl-6-ethylanilino)-propionic acid methyl ester with furan-(2)-carboxylic acid or one of the reactive derivatives thereof.

EXAMPLE 2

Manufacture of

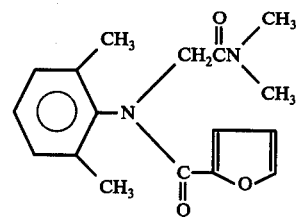

N-(dimethylaminocarbonylmethyl)-N-(furan-(2'')-carbonyl)-2,6-dimethylaniline.

28 g of the N-(1'-methoxycarbonyl-methyl)-N-(furan-(2'')-carbonyl)-2,6-dimethylaniline manufactured analogously to Example 1 (m.p. 98°–99° C) are stirred for 1 day at room temperature with 150 ml of 40% aqueous dimethylamine solution and 0.5 g of triethylenediamine.

Unreacted starting material is removed by performing extraction twice with ether and the aqueous phase is then concentrated by rotary evaporation. The residual viscous oil is crystallised by trituration with hexane.

The end product has a melting point of 142°–145° C after recrystallisation from hexane/tetrahydrofuran.

EXAMPLE 3

Manufacture of

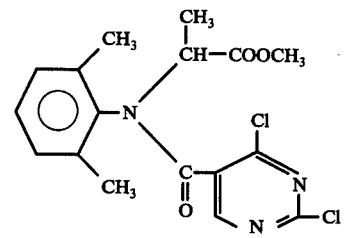

N-(1'-methoxycarbonylethyl)-N-(2'',4''-dichloropyrimidine-(5'')-carbonyl)-2,6-dimethylaniline.

With stirring, 25.4 g of 2,4-dichloropyrimidine-5-carboxylic acid chloride in 50 ml of chlorobenzene were added dropwise within 20 minutes to a mixture of 20.7 g of N-(1'-methoxycarbonylethyl)-2,6-dimethylaniline, 2 ml of dimethyl formamide and 150 ml of chlorobenzene, in the process of which the temperature rose by 10° C. The reaction mixture was then heated to 110° C and the hydrogen chloride which had formed was removed by passing in nitrogen. The solvent was evaporated off by rotary evaporation and the crude product was then crystallised by trituration with petroleum ether. The end product which was purified by recrystallisation from isopropanol had a melting point of 136°–137° C. The following compounds of the formula Ic ($R_1$ = 2-position) which are tri- or tetra-substituted in the phenyl nucleus are manufactured in this manner or by one of the methods indicated hereinabove.

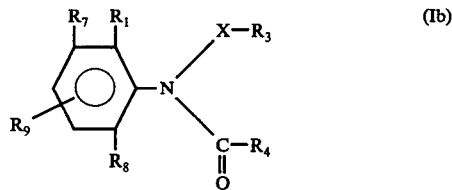

(Ib)

| Compound | $R_1$ | $R_7$ | $R_8$ | $R_9$ | —X—$R_3$ | $R_4$ | Physical constant |
|---|---|---|---|---|---|---|---|
| 1 | $CH_3$ | $CH_3$ | $CH_3$ | 5-$CH_3$ | —CH(CH$_3$)—COOCH$_3$ | furan | m.p. 83,5–85° C |
| 2 | $CH_3$ | $CH_3$ | $C_2H_5$ | H | —CH(CH$_3$)—COOCH$_3$ | furan | m.p. 110.5°–126° C |
| 3 | $C_2H_5$ | $CH_3$ | $CH_3$ | H | —CH(CH$_3$)—COOCH$_3$ | furan | b.p. 176°–177° C/ 0,05 Torr |
| 4 | Cl | H | Br | 4-Br | —CH(CH$_3$)—COOCH$_3$ | furan | b.p. 165–175° C/ 0,05 Torr |
| 5 | $CH_3$—O— | $CH_3$ | Cl | H | —CH(CH$_3$)—COOCH$_3$ | furan | oil |
| 6 | $CH_3$ | Br | $CH_3$ | H | —CH(CH$_3$)—COOCH$_3$ | furan | m.p. 83°–118° C |
| 7 | $CH_3$ | H | $CH_3$ | 4-$CH_3$ | —CH(CH$_3$)—COOCH$_3$ | furan | m.p. 113°–114° C |
| 8 | $CH_3$ | H | Br | 4-$CH_3$ | —CH(CH$_3$)—COOCH$_3$ | furan | m.p. 135–140° C |
| 9 | $CH_3$ | $CH_3$ | $CH_3$ | H | —CH(CH$_3$)—COOCH$_3$ | furan-Br | m.p. 88°–91° C |
| 10 | $CH_3$ | H | Br | 4-Br | —CH(CH$_3$)—COOCH$_3$ | furan | m.p. 134–138,5° C |
| 11 | $CH_3$ | $CH_3$ | $CH_3$ | H | —$CH_2$—CON($CH_3$)$_2$ | furan-Br | m.p. 132°–139° C |
| 12 | $CH_3$ | $CH_3$ | $CH_3$ | H | —CH(CH$_3$)—COOCH$_3$ | furan (H) | b.p. 171°–176° C/ 0,2 Torr |
| 13 | $CH_3$ | H | Br | 4-Cl | —CH(CH$_3$)—COOCH$_3$ | furan | m.p. 143–145° C |
| 14 | Br | $CH_3$ | $CH_3$ | 4-Br | —CH(CH$_3$)—COOCH$_3$ | furan | m.p. 114–122° C |
| 15 | $CH_3$ | $CH_3$ | $CH_3$ | H | —CH(CH$_3$)—COOCH$_3$ | 4,6-dichloropyrimidine | m.p. 126°–132° C |
| 16 | $CH_3$ | H | $C_2H_5$ | 4-Br | —CH(CH$_3$)—COOCH$_3$ | furan | m.p. 105–107° C |

-continued

| Compound | $R_1$ | $R_7$ | $R_8$ | $R_9$ | $-X-R_3$ | $R_4$ | Physical constant |
|---|---|---|---|---|---|---|---|
| 17 | $CH_3$ | H | $CH_3$ | 4-$CH_3$ | $-\underset{\underset{CH_3}{\mid}}{CH}-COOCH_3$ | 2,4-dichloro-5-methylpyrimidin-yl | m.p. 147°–150° C |
| 18 | $CH_3$ | H | $CH_3$ | 4-$CH_3$ | $-\underset{\underset{CH_3}{\mid}}{CH}-COOCH_3$ | 5-bromofuran-2-yl | m.p. 104°–107° C |
| 19 | $CH_3$ | $CH_3$ | $CH_3$ | 5-$CH_3$ | $-\underset{\underset{CH_3}{\mid}}{CH}-COOCH_3$ | tetrahydrofuran-2-yl | oil |
| 20 | $CH_3$ | H | $CH_3$ | 4-Cl | $-\underset{\underset{CH_3}{\mid}}{CH}-COOCH_3$ | furan-2-yl | m.p. 106°–110° C |
| 21 | $CH_3$ | H | $CH_3$ | 4-Br | $-\underset{\underset{CH_3}{\mid}}{CH}-COOCH_3$ | furan-2-yl | m.p. 113°–115° C |
| 22 | $CH_3$ | H | Cl | 4-Cl | $-\underset{\underset{CH_3}{\mid}}{CH}-COOCH_3$ | furan-2-yl | m.p. 125°–128° C |
| 23 | $CH_3$ | H | Cl | 4-Br | $-\underset{\underset{CH_3}{\mid}}{CH}-COOCH_3$ | furan-2-yl | m.p. 132°–134° C |
| 24 | $CH_3$ | H | $CH_3$ | 4-Cl | $-\underset{\underset{CH_3}{\mid}}{CH}-COOCH_3$ | 5-bromofuran-2-yl | m.p. 108°–111° C |

The compounds listed hereinafter are mono- or disubstituted in the phenyl nucleus. They include compounds of the formula

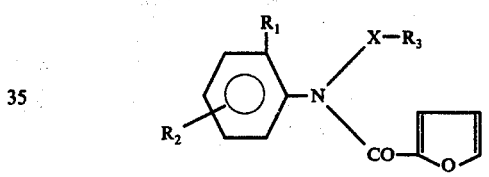

| Compound | $R_1$ | $R_2$ | $-X-R_3$ | Physical constant |
|---|---|---|---|---|
| 25 | $CH_3$ | 6-$CH_3$ | $-\underset{\underset{CH_3}{\mid}}{CH}-COO-C_2H_5$ | m.p. 90°–° C |
| 26 | $CH_3$ | H | $-\underset{\underset{CH_3}{\mid}}{CH}-COOCH_3$ | b.p. 126°–148° C/0.02 Torr |
| 27 | $CH_3$ | 3-$CH_3$ | $-\underset{\underset{CH_3}{\mid}}{CH}-COOCH_3$ | b.p. 151° C/0.03 Torr |
| 28 | $CH_3$ | 4-$CH_3$ | $-\underset{\underset{CH_3}{\mid}}{CH}-COOCH_3$ | m.p. 89°–91° C |
| 29 | $CH_3$ | 5-$CH_3$ | $-\underset{\underset{CH_3}{\mid}}{CH}-COOCH_3$ | m.p. 114°–116° C |
| 30 | $CH_3$ | 6-$C_2H_5$ | $-CH_2-COOCH_3$ | m.p. 91°–94° C |
| 31 | $CH_3$ | 6-Cl | $-\underset{\underset{CH_3}{\mid}}{CH}-COOC_2H_5$ | m.p. 112°–113° C |
| 32 | $CH_3$ | 6-$CH_3$ | $-\underset{\underset{CH_3}{\mid}}{CH}-CO-NH_2$ | m.p. 128°–130° C |
| 33 | Cl | 5-Cl | $-\underset{\underset{CH_3}{\mid}}{CH}-COOCH_3$ | m.p. 110°–112° C |
| 34 | $C_2H_5$ | 6-$C_2H_5$ | $-CH_2-CO-NH_2$ | m.p. 127°–128° C |
| 35 | $CH_3$ | 6-Cl | $-\underset{\underset{CH_3}{\mid}}{CH}-COOCH_3$ | m.p. 92°–93° C |
| 36 | $nC_4H_9-O-$ | H | $-\underset{\underset{CH_3}{\mid}}{CH}-COOCH_3$ | b.p. 170°–173° C/0.04 Torr |

-continued

| Compound | $R_1$ | $R_2$ | $-X-R_3$ | Physical constant |
|---|---|---|---|---|
| 37 | $CH_3$ | 6-$CH_3$ | $-CH(CH_3)-CO-NHCH_3$ | m.p. 141° – 143° C |
| 38 | iso-$C_3H_7$ | 6-iso$C_3H_7$ | $-CH(CH_3)-COOCH_3$ | m.p. 86° – 96° C |
| 39 | iso-$C_3H_7$ | H | $-CH(CH_3)-COOCH_3$ | b.p. 158° C/0.03 Torr |
| 40 | F | H | $-CH(CH_3)-COOCH_3$ | b.p. 150° C/0.03 Torr |
| 41 | Cl | H | $-CH(CH_3)-COOCH_3$ | b.p. 155° C/0.05 Torr |
| 42 | Cl | 6-Cl | $-CH(CH_3)-COOCH_3$ | m.p. 113° – 116° C |
| 43 | I | H | $-CH(CH_3)-COOCH_3$ | b.p. 145° C/0.2 Torr |
| 44 | Br | H | $-CH(CH_3)-COOCH_3$ | b.p. 145° C/0.05 Torr |
| 45 | $CH_3$ | 6-$CH_3$ | $-CH_2-COOCH_3$ | m.p. 98° – 99° C |
| 46 | $CH_3$ | 6-$CH_3$ | $-CH_2-CO-NHCH_3$ | m.p. 164° – 165° C |
| 47 | $CH_3$ | 6-$CH_3$ | $-CH_2-CO-N(CH_3)_2$ | m.p. 142° – 145° C |
| 48 | $CH_3$ | 4-$CH_3O-$ | $-CH(CH_3)-COOCH_3$ | b.p. 168° C/0.07 Torr |
| 49 | $CH_3$ | 4-sec.$C_4H_9O$ | $-CH(CH_3)-COOCH_3$ | b.p. 178° C/0.05 Torr |
| 50 | $C_2H_5$ | 6-$C_2H_5$ | $-CH_2-CO-N(CH_3)_2$ | m.p. 178° – 181° C |
| 51 | $C_2H_5$ | 6-$C_2H_5$ | $-CH_2-COOCH_3$ | m.p. 88° C |
| 52 | $C_2H_5$ | 6-$C_2H_5$ | $-CH_2-CO-NHC_2H_5$ | m.p. 158° – 159° C |
| 53 | $CH_3$ | 6-$C_2H_5$ | $-CH(CH_3)-COOCH_3$ | b.p. 162° – 163°/0.1 Torr |

Also the compounds of the general formula:

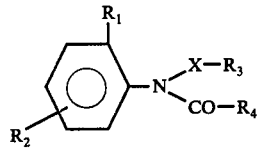

| Compound | $R_1$ | $R_2$ | $-X-R_3$ | $R_4$ | Physical constant |
|---|---|---|---|---|---|
| 54 | $CH_3$ | 6-$CH_3$ | $-CH(CH_3)-COOCH_3$ | pyridyl | m.p. 95° – 96° C |
| 55 | $CH_3$ | 6-Cl | $-CH(CH_3)-COOCH_3$ | pyridyl | m.p. 85° – 87° C |
| 56 | $CH_3$ | 6-Cl | $-CH(CH_3)-COOC_2H_5$ | pyridyl | m.p. 63° – 66° C |
| 57 | $CH_3$ | 6-$C_2H_5$ | $-CH_2-COOCH_3$ | pyridyl | m.p. 88° – 90° C |
| 58 | $CH_3$ | 6-$CH_3$ | $-CH_2-CON(CH_3)_2$ | pyridyl | m.p. 148° – 152° C |

-continued

| Compound | R₁ | R₂ | —X—R₃ | R₄ | Physical constant |
|---|---|---|---|---|---|
| 59 | CH₃ | 6-CH₃ | —CH(CH₃)—COOCH₃ | 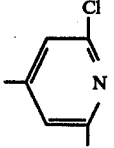 2,6-dichloropyridin-4-yl | m.p. 122° – 123° C |
| 60 | C₂H₅ | 6-C₂H₅ | —CH₂—CONH₂ | 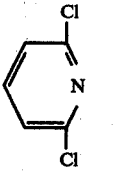 2,6-dichloropyridin-3-yl | m.p. 162° – 163° C |
| 61 | CH₃ | 6-Cl | —CH(CH₃)—COOCH₃ | 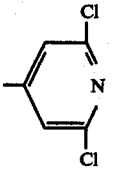 2,6-dichloropyridin-4-yl | m.p. 95° – 97° C |
| 62 | isoC₃H₇ | 6-isoC₃H₇ | —CH(CH₃)—COOCH₃ | 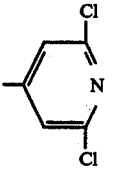 2,6-dichloropyridin-4-yl | m.p. 150° – 151° C |
| 63 | CH₃ | 6-CH₃ | —CH(CH₃)—COOCH₃ |  furyl | m.p. 97° – 98° C |
| 64 | CH₃ | 6-Cl | —CH(CH₃)—COOCH₃ |  furyl | m.p. 73° – 85° C |
| 65 | CH₃ | 6-C₂H₅ | —CH₂—COOCH₃ | 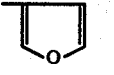 furyl | m.p. 76° – 77° C |
| 66 | CH₃ | 6-Cl | —CH(CH₃)—COOCH₃ | 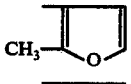 methylfuryl | m.p. 108° – 110° C |
| 67 | CH₃ | 6-CH₃ | —CH(CH₃)—COOCH₃ | 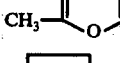 methylfuryl | m.p. 138° C |
| 68 | CH₃ | 6-CH₃ | —CH₂—COOCH₃ | 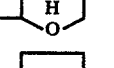 tetrahydrofuryl | m.p. 50 – 51° C |
| 69 | CH₃ | 6-CH₃ | —CH(CH₃)—COOCH₃ | 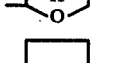 tetrahydrofuryl | m.p. 83 – 85° C |
| 70 | CH₃ | 6-CH₃ | —CH(CH₃)—COOCH₃ | 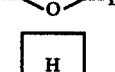 bromotetrahydrofuryl | oil |
| 71 | CH₃ | 6-Cl | —CH(CH₃)—COOCH₃ | 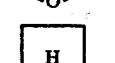 tetrahydrofuryl | m.p. 90 – 105° C |
| 72 | Cl | 6-Cl | —CH(CH₃)—COOCH₃ |  tetrahydrofuryl | oil |
| 73 | CH₃ | 6-CH₃ | —CH(CH₃)—COOCH₃ |  bromofuryl | m.p. 90° – 92° C |
| 74 | CH₃ | 6-Cl | —CH(CH₃)—COOCH₃ | 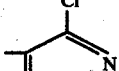 bromofuryl | m.p. 102° – 104° C |
| 75 | CH₃ | 6-CH₃ | —CH(CH₃)—COOCH₃ | 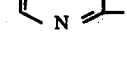 2,4-dichloropyrimidin-5-yl | m.p. 136° – 137° C |

-continued

| Compound | $R_1$ | $R_2$ | $-X-R_3$ | $R_4$ | Physical constant |
|---|---|---|---|---|---|
| 76 | $CH_3$ | 6-Cl | $-CH(CH_3)-COOCH_3$ | 4-(2-chloropyrimidinyl) | m.p. 142° – 145° C |
| 77 | $CH_3$ | 6-$CH_3$ | $-CH_2-CON(CH_3)_2$ | 4-(2,5-dichloropyrimidinyl) | m.p. 172° – 174° C |

The compounds of the formula I can be used by themselves or together with suitable carriers and/or other additives. Suitable carriers and additives can be solid or liquid and correspond to the customary substances used in formulation technology, for example natural or regenerated mineral substances, solvents, dispersants, wetting agents, stickers, thickeners, binders or fertilisers. The amount of active substance in commercially useful compositions is between 0.1 and 90%.

The compounds of the formula I can be applied in the following process forms (the percentages by weight in brackets denote the advantageous amounts of active substance): solid forms: dusts and tracking agents (up to 10%); granules, coated granules, impregnated granules and homogeneous granules (1 to 80%);
liquid forms:
a. active substance concentrates which are dispersible in water:
   wettable powders and pastes (25-90% in the commercial pack, 0.01 to 15% in ready for use solution);
   emulsion concentrates and concentrated solutions (10 to 50%; 0.01 to 15% in ready for use solution);
b. solutions (0.1 to 20%).

The active substances of the formula I can be formulated, for example, as follows:

Dusts: The following substances are used to manufacture (a) a 50% and (b) a 2% dust:

a.
5 parts of active substance
95 parts of talcum;

b.
2 parts of active substance
1 part of highly disperse silicic acid
97 parts of talcum.

The active substances are mixed with the carriers and ground and in this form can be processed to dusts for application.

Granules: The following substances are used to manufacture 5% granules:
5 parts of active substance
0.25 part of epichlorohydrin
0.25 part of cetyl polyglycol ether
3.50 parts of polyethylene glycol
91 parts of kaolin (particle size 0.3 – 0.8 mm).

The active substance is mixed with the epichlorohydrin and the mixture is dissolved in 6 parts of acetone. Then polyethylene glycol and cetyl polyglycol ether are added. The resultant solution is sprayed on kaolin and the acetone is evaporated in vacuo. Such micro granules are advantageously used for combating soil fungi.

Wettable powders: The following constituents are used to manufacture (a) a 70% (b) a 40%, (c) and (d) a 25% and (e) a 10% wettable powder:

a.
70 parts of active substance
5 parts of sodium dibutyl naphthylsulphonate
3 parts of naphthalenesulphonic acid/phenolsulphonic acid/formaldehyde condensate (3:2:1)
10 parts of kaolin
12 parts of Champagne chalk b.
40 parts of active substance
5 parts of sodium lignin sulphonate
1 part of sodium dibutylnaphthalenesulphonic acid
54 parts of silicic acid c.
25 parts of active substance
4.5 parts of calcium lignin sulphonate
1.9 parts of a Champagne chalk/hydroxyethyl cellulose mixture (1:1)
1.5 parts of sodium dibutylnaphthalenesulphonate
19.5 parts of silicic acid
19.5 parts of Champagne chalk
28.1 parts of kaolin d.
25 parts of active substance
2.5 parts of isooctylphenoxy-polyethylene-ethanol
1.7 parts of a Champagne chalk/hydroxyethyl cellulose mixture (1:1)
8.3 parts of sodium aluminium silicate
16.3 parts of kieselguhr
46 parts of kaolin e.
10 parts of active substance
3 parts of a mixture of the sodium salts of saturated fatty alcohol sulphates
5 parts of naphthalenesulphonic acid/formaldehyde condensate
82 parts of kaolin.

The active substances are intimately mixed in suitable mixers with the additives and ground in appropriate mills and roolers. Wettable powders of excellent wettability and suspension power are obtained. These wettable powders can be diluted with water to give suspensions of every desired concentration and can be used in particular for application to leaves.

Emulsifiable concentrates: The following substances are used to manufacture a 25% emulsifiable concentrate:

25 parts of active substance
2.5 parts of epoxidised vegetable oil
10 parts of an alkylarylsulphonate/fatty alcohol polyglycol ether mixture
5 parts of dimethyl formamide
57.5 parts of xylene By diluting such concentrates with water it is possible to manufacture emulsions of every desired concentration which are especially suitable for application to leaves.

EXAMPLE 4

Action against *Phytophthora infestans* on *Solanum lycopersicum* (tomatoes).

Ia. Residual preventive action

Solanum lycopersicum plants of the "Roter Gnom" variety are infected when 3 weeks old with a zoospore suspension of Phytophthora infestans after they have been sprayed with a broth prepared from the active substance processed to a wettable powder and containing 0.05% of active substance, and dried. They are then kept for 6 days in a climatic chamber at 18° to 20° C and high humidity, which is produced with an artificial wet fog. After this time typical leaf specks appear. Their number and size are the criterion for evaluating the tested substance.

Ib. Curative action

"Roter Gnom" tomato plants are sprayed when 3 weeks old with a zoospore suspension of the fungus and incubated in a climatic chamber at 18° to 20° C and saturated humidity. The humidifying is interrupted after 24 hours. After the plants have been dried, they are sprayed with a broth which contains the active substance formulated as wettable powder in a concentration of 0.05%. After the spray coating has dried, the plants are again kept in the humid chamber for 4 days. Size and number of the typical leaf specks which have occurred during this time are the criterion for evaluating the effectiveness of the tested substances.

II. Preventive-systemic action

The active substance is applied as wettable powder in a concentration of 0.05% (referred to the volume of the soil) to the surface of the soil of 3 week old "Roter Gnom" tomatoes in pots. Three days later the underside of the leaves of the plants are sprayed with a zoospore suspension of Phytophthora infestans. The plants are then kept for 5 days in a spray chamber at 18° to 20° C and saturated humidity, after which time typical leaf specks form. The size and number of the specks serve as criterion for evaluating the effectiveness of the tested substances.

In the test of Example 4 the compounds of formula I exhibit the following strong action against the leave-fungus (average values).

Table

| Compound | Fungus infection in % |
|---|---|
| 1 | 0 - 5 % |
| 2 | <20 % |
| 3 | <20 % |
| 6 | <20 % |
| 7 | <20 % |
| 9 | <20 % |
| 12 | <20 % |
| 13 | <20 % |
| 14 | <20 % |
| 15 | <20 % |
| 16 | <20 % |
| 17 | 20 - 40 % |
| 19 | <20 % |
| 25 | 0 - 5 % |
| 27 | <20 % |
| 28 | 0 - 5 % |
| 29 | <20 % |
| 31 | <20 % |
| 32 | 0 - 5 % |
| 35 | <20 % |
| 42 | <20 % |
| 53 | 0 - 5 % |
| 68 | <20 % |
| 69 | <20 % |
| 71 | <20 % |
| 73 | 0 - 5 % |
| 75 | <20 % |

EXAMPLE 5

Action against *Plasmopara viticola* (Bert. et Curt.) (Berl. et De Toni) on vines a. Residual prevention action Vine cuttings of the variety "Chasselas" were reared in a greenhouse. Three plants in the 10 leaf stage were sprayed with a 0.05% broth prepared from the active substance and formulated as a wettable powder. After the coating layer had dried, the plants were infected on the underside of the leaves with the spore suspension of the fungus. The plants were subsequently kept for 8 days in a humid chamber, after which time symptoms of the disease were visible on the control plants. The number and size of the infected areas on the treated plants served as criterion for evaluating the effectiveness of the tested active substances.

b. Curative action

Vine cuttings of the variety "Chasselas" were reared in a greenhouse and infected in the 10 leaf stage with a spore suspension of Plasmopara viticola on the underside of the leaves. After they had been kept for 24 hours in a humid chamber, the plants were sprayed with an active substance broth (0.05%) prepared from a wettable powder of the active substance. The plants were then kept for a further 7 days in a humid chamber, after which time the symptoms of the disease were visible on the control plants. The size and number of the infected areas served as criterion for evaluating the effectiveness of the tested substances.

In both these tests the compounds of the formula I exhibited a predominantly leaf-fungicidal action. Without exception, the compounds listed in the Table of Example 4 reduced the fungus infection to <20% and in some cases almost no infection occurred (0 - 5%).

EXAMPLE 6

Action against *Erysiphe graminis* on *Hordeum vulgare* (barley)

Residual protective action

Barley plants about 8 cm in height were sprayed with a spray broth (0.05% active substance) prepared from a wettable powder of the active substance. After 48 hours the treated plants were dusted with conidia of the fungus. The infected barley plants were stood in a greenhouse at about 22° C and the fungus infection was evaluated 10 days later.

A number of the compounds of the formula I, e.g. compounds 55 and 56, effect in this test a reduction of the fungus infection to <20%.

EXAMPLE 7

Action against *Pythium debaryanum* in *Beta vulgaris* (sugar beet)

a. Action after soil application

The fungus is cultivated on sterile oat kernels and added to a mixture of earth and sand. Flower pots are filled with the infected soil in which sugar beet seeds are then sown. Immediately after sowing, the test preparations formulated as wettable powders are poured in the form of aqueous suspensions over the soil (0.002% active substance referred to the volume of the soil). The pots are then stood for 2-3 weeks in a greenhouse at 20°-24° C. The soil is kept uniformly moist by gently spraying it with water. The emergence of the sugar beet plants as well as the number of healthy and sick plants are ascertained in evaluating the tests.

b. Action after seed dressing

The fungus is cultivated on sterile oat kernels and added to a mixture of earth and sand. Flower pots are filled with the infected soil and sugar beet seeds which have been treated with the test preparations formulated as seed dressing powders are sown therein (0.1% active substance referred to the weight of the seeds). The pots are then stood in a greenhouse for 2-3 weeks at 20°-24° C. The soil is kept uniformly moist by gently spraying it with water. The emergence of the sugar beet plants as well as the number of healthy and sick plants are ascertained.

Under the conditions of both test (a) and test (b), more than 85% of the sugar beet plants emerged after treatment with the active substances of the formula I and had a healthy appearance. Less than 20% of the untreated control plants emerged and their appearance was in part sickly.

I claim:

1. A compound of the formula

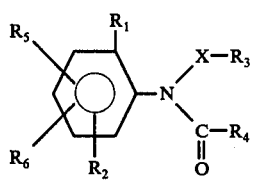

wherein $R_1$ represents methyl, $R_2$ is in ortho-position to the amino group and represents methyl, ethyl or chlorine, —X—$R_3$ is

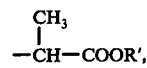

$R_5$ represents hydrogen, alkyl of 1 to 3 carbon atoms or halogen, $R_6$ represents hydrogen or methyl, the total number of carbon atoms of the substituents $R_1$, $R_2$, $R_5$ and $R_6$ in the phenyl ring not exceeding 8, R' is hydrogen, methyl or ethyl, and $R_4$ is 2-furanyl or 2-tetrahydrofuranyl which may be substituted by methyl or halogen, with the proviso that the phenyl ring contains a further substituent other than hydrogen if it is substituted in 2,6- or in 2,3,6-position by methyl and if at the same time $R_4$ represents the 2-furanyl radical and —X—$R_3$ represents the α-propionic acid methyl ester.

2. A compound of the formula I according to claim 1, wherein $R_4$ represents 2-furanyl or 2-tetrahydrofuranyl.

3. A compound of the formula I according to claim 2, wherein —X—$R_3$ represents the α-propionic acid methyl ester group and wherein the total number of carbon atoms of the substituents $R_1$, $R_2$, $R_5$ and $R_6$ does not exceed 4.

4. A compound of the formula I according to claim 3 which are derived from 2,6-dimethylaniline, 2,4,6-trimethyl-aniline, 2,3,5,6-tetramethylaniline or from a 2,6-dimethylaniline derivative which contains in the phenyl nucleus a third substituent $R_5$ or $R_6$ other than hydrogen.

5. N-(1'-methoxycarbonyl-ethyl)-N-(furan-(2″)-carbonyl)-2,3,5,6-tetramethylaniline of the formula

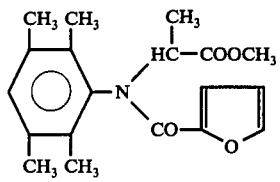

according to claim 3.

6. N-(1'-methoxycarbonyl-ethyl)-N-(furan(2″)-carbonyl)-2,6-dimethyl-4-chloroaniline according to claim 1.

7. N-(1'-methoxycarbonyl-ethyl)-N-(furan(2″)-carbonyl)-2,4,6-trimethyl-aniline according to claim 1.

8. N-(1'-methoxycarbonyl-ethyl)-N-(tetrahydrofuran(2″)-carbonyl)-2,6-dimethyl-aniline according to claim 1.

9. N-(1'-methoxycarbonyl-ethyl)-N-(5″-bromofuranyl(2″)-carbonyl)-2,6-dimethylaniline according to claim 1.

10. The enantiomeric D-configurations of the compounds according to claim 1.

11. N-(1'methoxycarbonyl-ethyl)-N-(furan(2″)-carbonyl)-2,6-dimethyl-3-bromoaniline according to claim 1.

12. N-(1'-methoxycarbonyl-ethyl)-N-(tetrahydrofuran (2″)-carbonyl)-2,3,6-trimethyl-aniline according to claim 1.

13. N-(1'-methoxycarbonyl-ethyl)-N-(tetrahydrofuran(2″)-carbonyl)-2,3,5,6-tetramethyl-aniline according to claim 1.

14. A phytofungicidal composition comprising as active substance a phytofungicidally effective amount of a compound according to claim 1, together with a suitable carrier therefor.

15. A phytofungicidal composition comprising as active substance a phytofungicidally effective amount of a compound of claim 4, together with a suitable carrier therefore.

16. A method of combatting phytopathogenic fungi which comprises applying to the locus thereof a fungicidally effective amount of a compound of claim 1.

17. The method of combatting phytopathogenic fungi which comprises applying to the locus thereof a fungicidally effective amount of a compound of claim 2.

* * * * *